United States Patent
Tang

(10) Patent No.: US 12,337,325 B2
(45) Date of Patent: Jun. 24, 2025

(54) NUCLEIC ACID TEST KIT AND PREPARATION PROCESS THEREOF

(71) Applicant: GUANGZHOU DEAOU GENE TECHNOLOGY CO., LTD, Guangzhou (CN)

(72) Inventor: Xuyun Tang, Guangzhou (CN)

(73) Assignee: GUANGZHOU DEAOU GENE TECHNOLOGY CO., LTD, Guangzhou (CN)

( * ) Notice: Subject to any disclaimer, the term of this patent is extended or adjusted under 35 U.S.C. 154(b) by 0 days.

(21) Appl. No.: 18/829,330

(22) Filed: Sep. 10, 2024

(65) Prior Publication Data
US 2024/0424497 A1 Dec. 26, 2024

Related U.S. Application Data

(63) Continuation of application No. PCT/CN2022/098129, filed on Jun. 10, 2022.

(30) Foreign Application Priority Data

Mar. 13, 2022 (CN) .......................... 202210244658.1

(51) Int. Cl.
*B01L 7/00* (2006.01)
*C12Q 1/6806* (2018.01)
*C12Q 1/686* (2018.01)

(52) U.S. Cl.
CPC .............. *B01L 7/52* (2013.01); *C12Q 1/6806* (2013.01); *C12Q 1/686* (2013.01); *B01L 2200/0689* (2013.01); *B01L 2300/041* (2013.01); *B01L 2300/0832* (2013.01)

(58) Field of Classification Search
None
See application file for complete search history.

(56) References Cited

U.S. PATENT DOCUMENTS

2018/0071728 A1* 3/2018 Liang ........................ B01L 7/52

FOREIGN PATENT DOCUMENTS

CN 214991576 U * 12/2021

* cited by examiner

*Primary Examiner* — Matthew D Krcha
(74) *Attorney, Agent, or Firm* — Andrew C. Cheng

(57) ABSTRACT

A nucleic acid test kit includes a lower circular fixing cover, a circular kit arranged on the lower circular fixing cover, a sealing film arranged at a top of the circular kit, and a lower lid arranged at a lower end of the sealing film. The bottom of the lower lid is pressed against the lower end of the sealing film, and a bottom of the sealing film is pressed against the top of the circular kit; and first bolts are rotatably connected to the lower circular fixing cover, and the first bolt is in threaded connection with the lower lid through first threaded hole. Air leakage detection can be performed after encapsulation is completed, which significantly improves the quality of encapsulation compared to traditional detection kits and increases encapsulation efficiency. The sealing film can block aerosol leakage from the kit, effectively preventing cross-contamination.

9 Claims, 9 Drawing Sheets

NUCLEIC ACID TEST KIT AND PREPARATION PROCESS THEREOF

FIELD

The invention relates to the technical field of nucleic acid test kits, in particular to a nucleic acid test kit and a preparation process thereof.

BACKGROUND

Nucleic acids are the carriers of genetic information in living organisms and are essential components of all known life forms. The two main classes of nucleic acids are DNA and RNA, which are primarily found in the cell nucleus and exist in a state bound to proteins. As the rapid development of molecular biology, research and analysis of nucleic acids have become increasingly prevalent and applied in diverse fields, including clinical diagnosis, food safety, environmental monitoring, and agriculture, forestry, and animal husbandry. Polymerase chain reaction (PCR) technology, a technique for rapid in vitro amplification of DNA, can be applied to fundamental research such as gene isolation, cloning, and nucleic acid sequence analysis. Moreover, it has proven valuable in any setting where DNA or RNA is present, such as in disease diagnosis.

Nucleic acid analysis technology, a powerful molecular diagnostic tool, plays a crucial role in pathogen diagnosis, infectious disease prevention, and disease monitoring and treatment. Compared to conventional immunological diagnostic methods, nucleic acid analysis has significant advantages in terms of high specificity and sensitivity. However, the low concentration of most target genes makes direct analysis and detection challenging. Therefore, nucleic acid analysis methods based on nucleic acid amplification principles, such as PCR and LAMP, have become the primary tools for nucleic acid analysis. The complete process typically involves three stages: nucleic acid extraction, nucleic acid amplification, and nucleic acid detection. Existing nucleic acid test kits often fail to integrate nucleic acid extraction and detection into a single closed system, leading to potential aerosol cross-contamination of samples during separate extraction and detection steps. This can result in false-positive results in subsequent nucleic acid tests and lower detection efficiency. Therefore, there is a need for a nucleic acid test kit and its preparation process to address these technical problems.

SUMMARY

In order to solve the above technical problems, the invention provides an improved nucleic acid test kit and a preparation process thereof.

In one aspect, the present invention provides a nucleic acid test kit which comprises a lower circular fixing cover; a circular kit arranged on an inner side of the lower circular fixing cover, a middle part of the circular kit being provided with a metal bar storage hole, a sealing film arranged at a top of the circular kit, and a lower lid arranged at a lower end of the sealing film, wherein a bottom of the lower lid is pressed against the lower end of the sealing film, and a bottom of the sealing film is pressed against the top of the circular kit; first bolts rotatably connected to an outer side of the lower circular fixing cover in an equidistant manner through bearings, the first bolt being in threaded connection with the lower lid through a first threaded hole; an upper cover arranged above the sealing film; and an upper circular fixing cover fixed to an outer wall of the upper cover. One side of the circular kit is provided with a sample adding port, a rubber plug is connected to a middle part of the sample adding port in an interference manner; a metal bar is fixed to a middle part of the upper cover, and a lower end of the metal bar is inserted into the metal bar storage hole; an upper end of the sealing film is provided with an upper lid, a top of the upper lid is pressed against the upper end of the sealing film, and a top of the sealing film is pressed against a bottom of the upper cover; second bolts are rotatably connected to an outer ring of the upper circular fixing cover in an equidistant manner through bearings, and the second bolts are in threaded connection with the upper lid through second threaded holes; and one side of the circular kit is provided with a mounting hole, a bottom of the circular kit is fixedly provided with a PCR tube located outside the mounting hole, and an pre-embedded tube component is arranged in an inner side of the mounting hole; and a side, away from the PCR tube, of the circular kit is provided with shallow tubes in an equidistant manner, a U-shaped aluminum foil film is arranged on a side, close to the shallow tubes, of the top of the circular kit, a detection hole is formed in one side of the upper cover, and a detection plug is connected to an inner wall of the detection hole in an interference manner.

Preferably, a first connecting mechanism is fixed to a bottom of the lower circular fixing cover, the first connecting mechanism is configured for driving the first bolts to rotate simultaneously, a second connecting mechanism is connected to a top of the upper circular fixing cover, and the second connecting mechanism is configured for driving the second bolts to rotate simultaneously.

Preferably, the pre-embedded tube component comprises an embedded tube body, an aluminum foil film and an aluminum foil film, the embedded tube body is arranged on an inner wall of the mounting hole, the aluminum foil film fixed to a bottom of the embedded tube body by heat seal, the aluminum foil film is fixed to a top of the embedded tube body by heat seal, and a bottom of the aluminum foil film pressed against a top of the PCR tube.

Preferably, the first connecting mechanism comprises a bottom connecting plate, an internal ring gear, first connecting shafts, first gears, a worm gear ring, supporting blocks, a worm and a first rotating wheel; and the bottom connecting plate is fixed to a bottom of the lower circular fixing cover, the internal ring gear is rotatably connected to a lower surface of the bottom connecting plate through a bearing, each of the first connecting shafts is fixed to a middle part of a lower surface of a corresponding one of the first bolts, and each of the first gears is fixed to a middle part of a corresponding one of first connecting shafts; the first gears are meshed with the internal ring gear, and the worm gear ring is fixed to a bottom of the internal ring gear; and the supporting blocks are symmetrically fixed to one side of a lower surface of the bottom connecting plate, the worm is rotatably connected between the two supporting blocks through a bearing, the worm is meshed with the worm gear ring, and one end of the worm passes through the supporting blocks and is fixed with the first rotating wheel.

Preferably, first positioning columns are fixed to a top of the lower circular fixing cover in an equidistant manner, first positioning sleeves are fixed to an outer wall of the lower lid in an equidistant manner, and the first positioning columns are fitted into the first positioning sleeves respectively.

Preferably, the second connecting mechanism comprises second connecting shafts, second gears, a rotating ring, gear ring and a second rotating wheel; each of the second connecting shafts is fixed to a middle part of an upper surface of a corresponding one of the second bolts, and each of the second gears is fixed to an upper end of a corresponding one of the second connecting shafts; the rotating ring is rotatably connected to a middle part of an upper surface of the upper circular fixing cover through a bearing; the gear ring is fixed to an outer wall of an upper end of the rotating ring; the second gears are engaged with the gear ring; and the second rotating wheel is fixed to a top of one of the second connecting shafts on one side of the upper circular fixing cover.

Preferably, second positioning columns are fixed to an outer wall of the upper circular fixing cover in an equidistant manner, second positioning sleeves are fixed to an outer wall of the upper lid in an equidistant manner, and the second positioning columns are fitted into the second positioning sleeves respectively.

Preferably, the first rotating wheel and the second rotating wheel are both configured in a plum blossom shape; and a top of the first positioning column and a bottom of the second positioning column are both provided with chamfers.

Preferably, supporting columns are fixed to a bottom of the bottom connecting plate in an equidistant manner, and a rubber friction pad is fixed to a bottom of the supporting column.

Preferably, the sealing film comprises an elastic film or a non-elastic film.

In another aspect, the present invention provides a preparation process of the nucleic acid test kit. The preparation process comprises the following steps:
(1) sealing the sample adding port with the rubber plug, and encapsulating a nucleic acid extraction reagent and magnetic beads in the circular kit with the U-shaped aluminum foil film the nucleic acid extraction reagent and the magnetic beads being placed in corresponding storage ports of the circular kit, and the magnetic beads being able to be replaced with magnetic bead liquid;
(2) adding liquid or solid reagents into the PCR tube, and then pressing the pre-embedded tube component into the mounting hole, the order of steps and being reversible;
(3) bonding the sealing film to the top of the circular kit and the bottom of the upper cover, followed by pressing and securing;
(4) introducing air from an external air source through the detection hole in the upper cover to test the seal tightness of the sealing film; and
(5) if no leakage is detected, sealing the detection hole in the upper cover with the detection plug.

Preferably, a desiccant is provided in an interior space surrounded by the sealing film, and the desiccant is located on the upper cover or a base without affecting the movement of the metal bar (10) and an encapsulating position of the reagent.

Preferably, a thickness of a wall of the PCR tube is 0.1-1.5 mm, and a light transmittance of the wall is not less than 60%.

As a preferred embodiment of the invention, a desiccant is fixed in the sealing film, and the desiccant is located on the upper cover or a base without affecting the movement of the metal bar and an encapsulating position of the reagent; and an outer wall thickness of the PCR tube is 0.1-1.5 mm, and the light transmittance is not less than 60% to ensure that it is able to pass the optical detection.

An upper surface of the U-shaped aluminum foil film does not react with the stored reagent, and a PP plastic film is attached to a lower surface, which can be stored in contact with the liquid and solid in the shallow tubes. The aluminum foil film at the top of the embedded tube body is a single-sided contact reagent. The aluminum foil film at the bottom is a double-sided contact reagent. The body of the pre-embedded tube component is sealed in the following order: first, the bottom of the body is sealed by the bottom aluminum foil film, then the embedded reagent is fed into the body, and the top of the body is sealed by the top aluminum foil film. The bottom liquid or solid reagent is placed in the PCR tube, and then the bottom surface of the bottom aluminum foil film is cleaned and the pre-embedded tube component is placed in the mounting hole to seal the PCR tube.

Compared with the prior art, the nucleic acid test kit and the preparation process thereof provided by the invention have the following beneficial effects.
1. The nucleic acid test kit provided by the invention greatly improves the efficiency of encapsulating nucleic acid detection reagents, and makes it easier for people to operate. Meanwhile, it can perform air leakage detection at the end of encapsulation, significantly enhancing the quality of encapsulation compared to traditional detection kits.
2. The nucleic acid test kit provided by the invention comprises a sealing film that is capable of blocking aerosol leakage from the kit during nucleic acid extraction, amplification reaction, and fluorescence detection processes, effectively preventing cross-contamination.
3. The nucleic acid test kit provided by the invention ensures a sealed environment of a nucleic acid test reagent device during the entire process, including nucleic acid extraction, amplification, and detection, reducing the risk of sample cross-contamination and effectively improving the nucleic acid testing efficiency.

Figure 1:
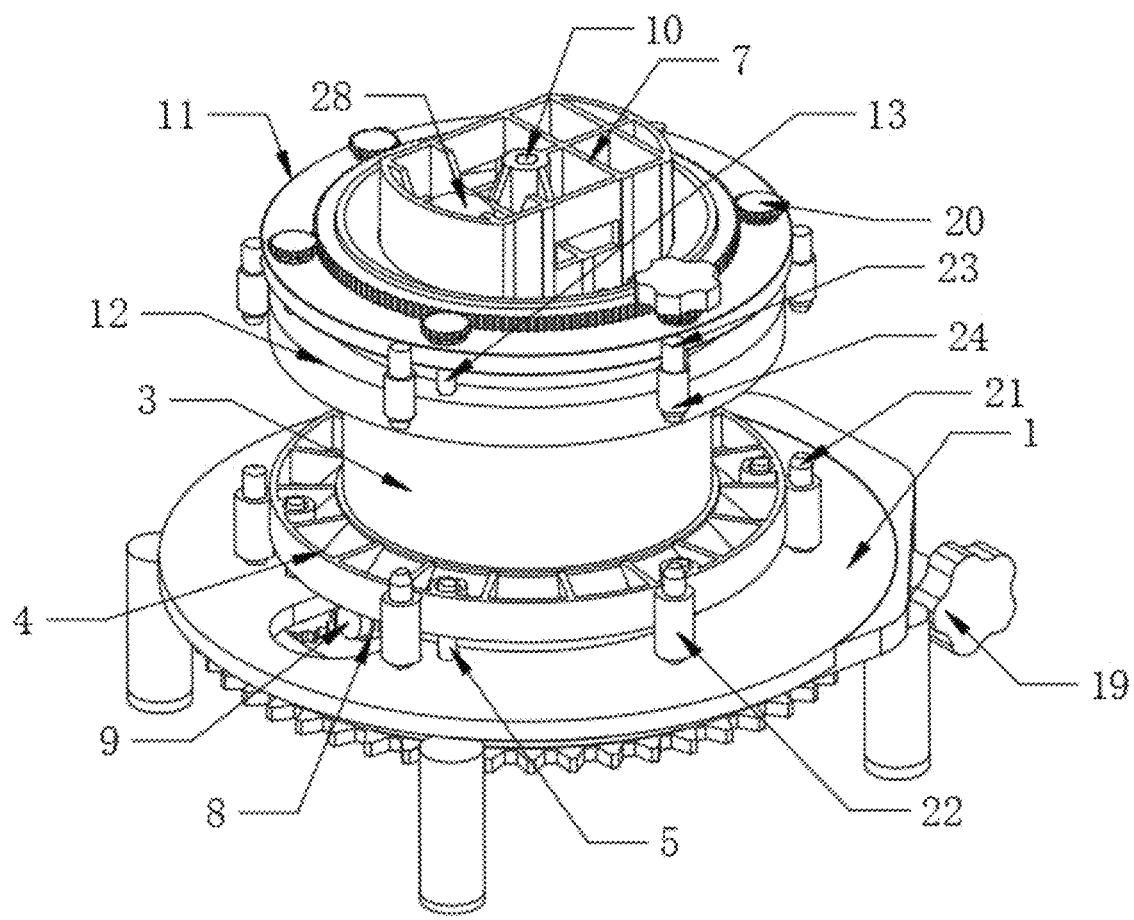
FIG. 1 is a schematic diagram of an overall structure according to the invention.
Figure 2:
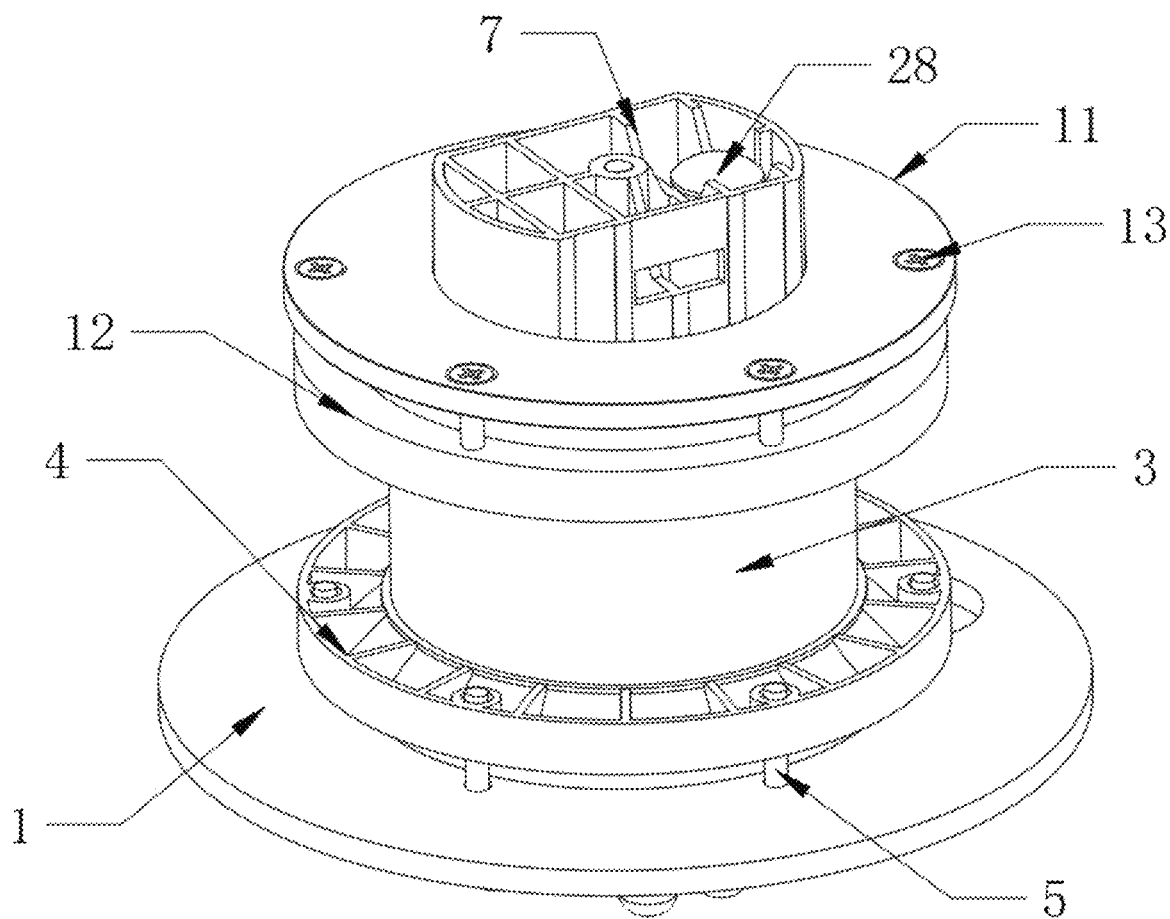
FIG. 2 is a schematic diagram of the position and structure of an upper lid according to the invention.
Figure 3:
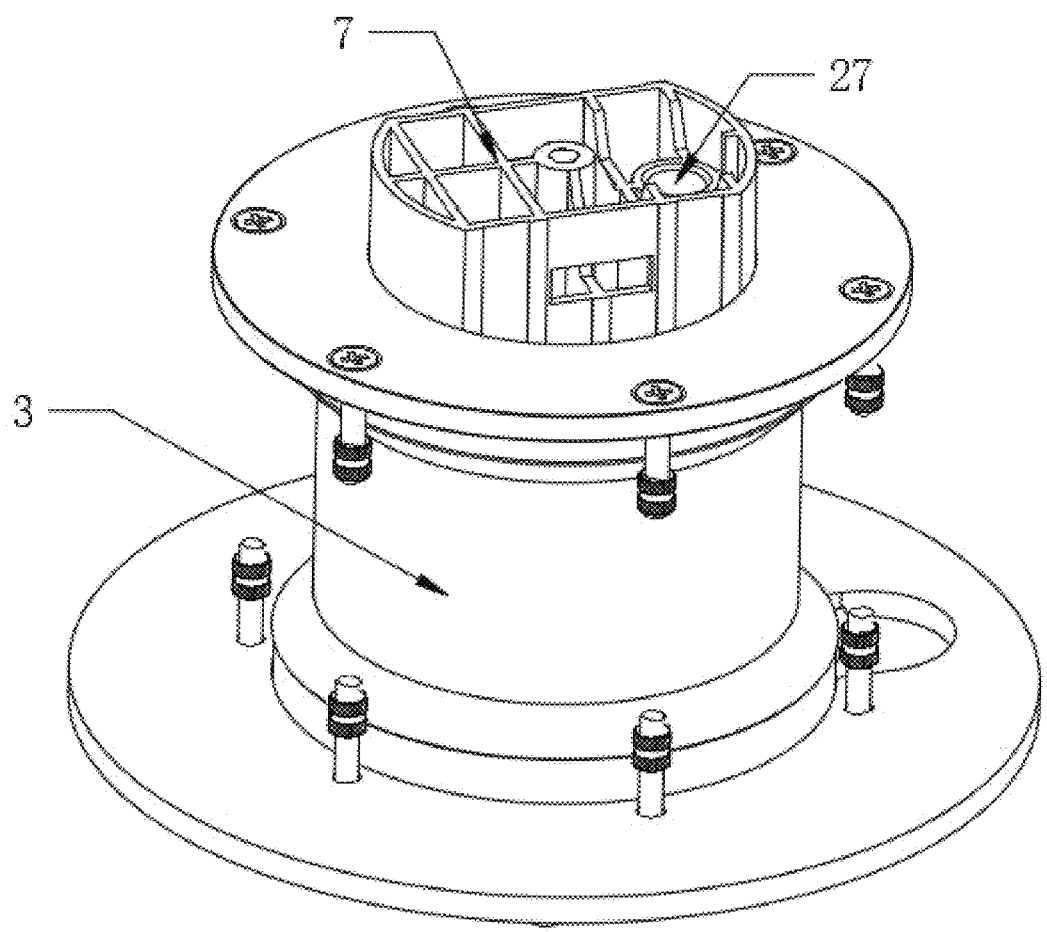
FIG. 3 is a schematic diagram of the shape and structure of a sealing film according to the invention.
Figure 4:
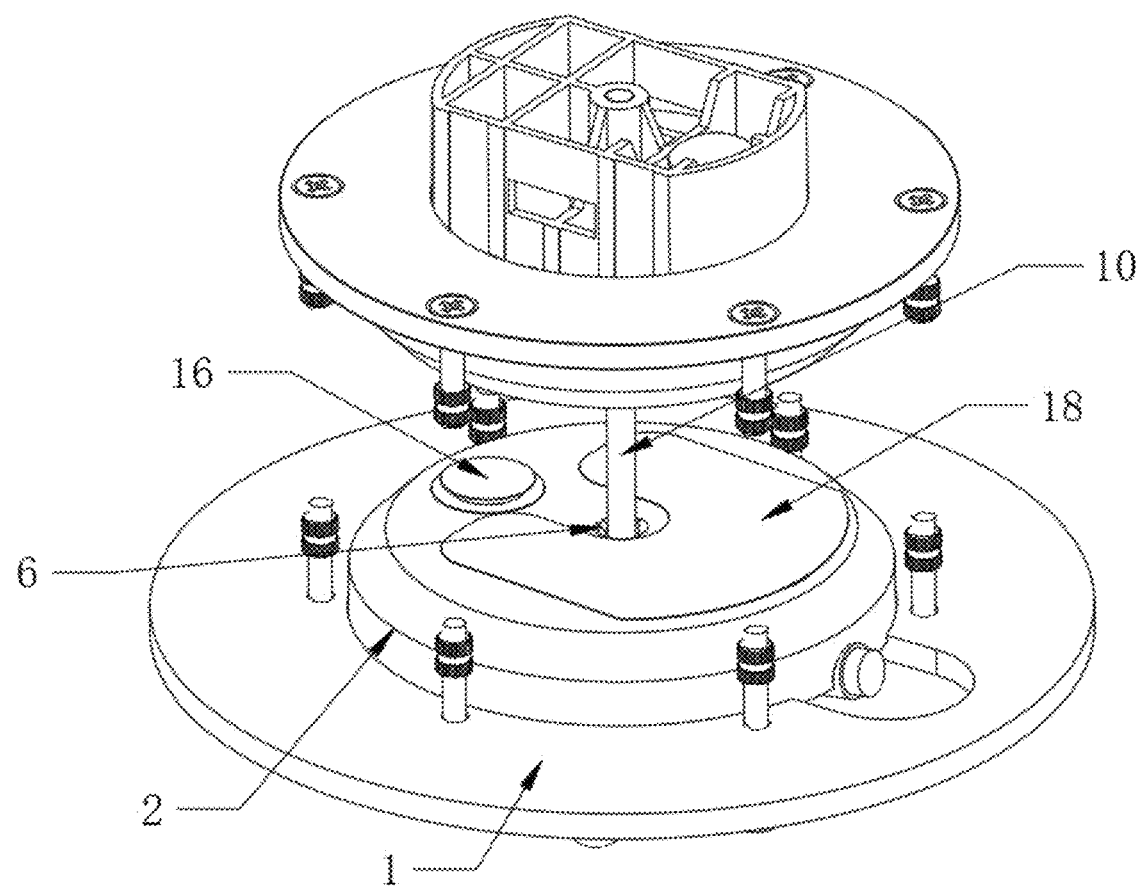
FIG. 4 is a schematic diagram of the position and structure of a metal bar storage hole according to the invention.
Figure 5:
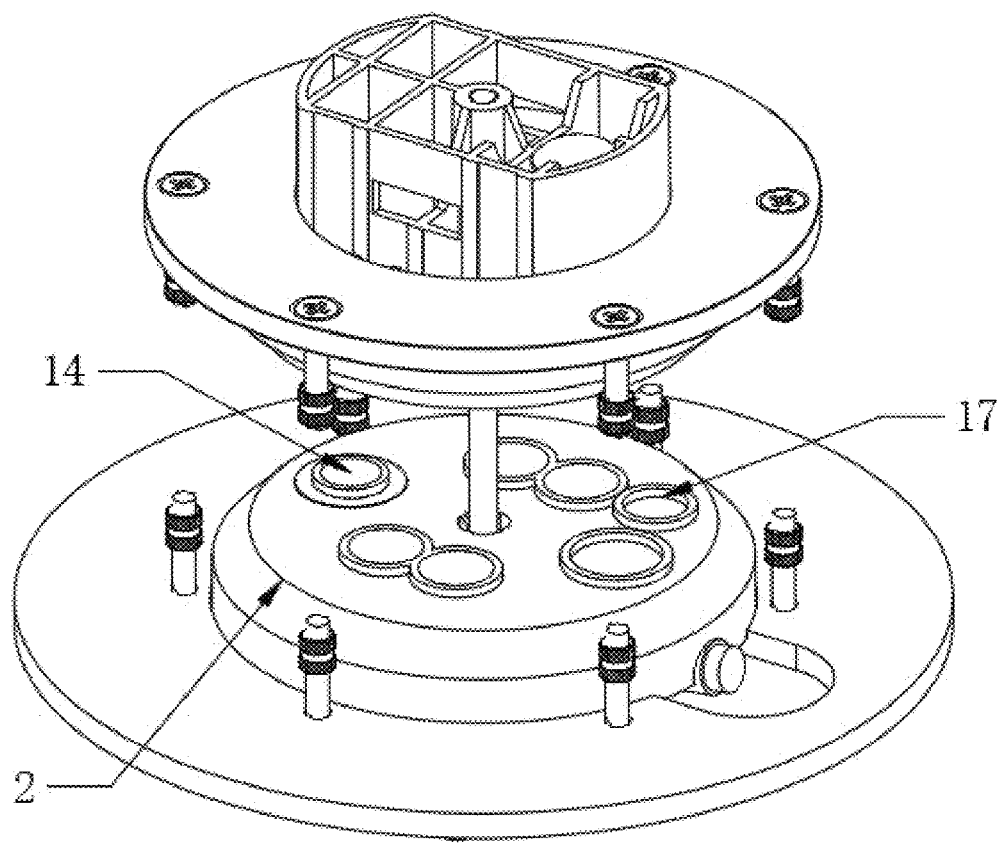
FIG. 5 is a schematic diagram of the position and structure of a mounting hole according to the invention.
Figure 6:
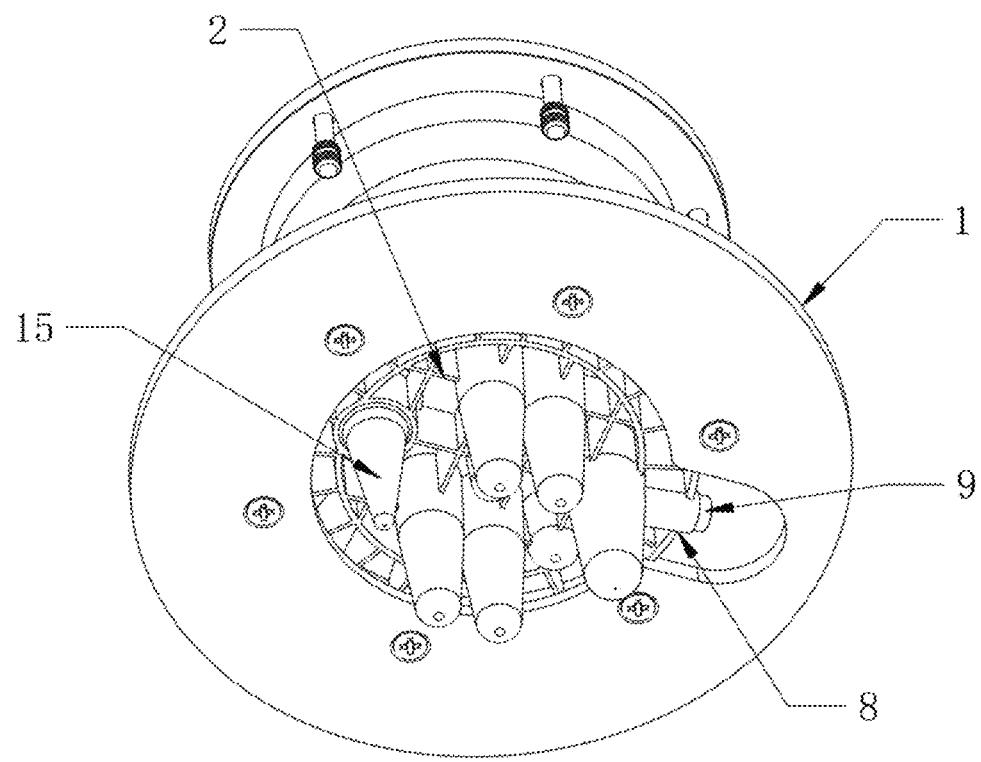
FIG. 6 is a schematic diagram of the position and structure of a PCR tube according to the invention.

Description of reference numerals: 1. lower circular fixing cover; 2. circular kit; 3. scaling film; 4. lower lid; 5. first bolt; 6. metal bar storage hole; 7. upper cover; 8. sample adding port; 9. rubber plug; 10. metal bar; 11. upper circular fixing cover; 12. upper lid; 13. second bolt; 14. embedded tube assembly hole; 15. PCR tube; 16. embedded tube component; 161. embedded tube body; 162. aluminum foil film B; 163. aluminum foil film A; 17. shallow tube; 18. U-shaped aluminum foil film; 19. first connecting mechanism; 191. bottom connecting plate; 192. internal ring gear; 193. first connecting shaft; 194. first gear; 195, worm gear ring; 196. supporting block; 197. worm; 198. first rotating wheel; 20. second connecting mechanism; 201. second connecting shaft; 202. second gear; 203. rotating ring; 204. gear ring; 205. second rotating wheel; 21. first positioning column; 22. first positioning sleeve; 23. second positioning column; 24. second positioning sleeve; 25. supporting column; 26. rubber friction pad; 27. detection hole; 28. detection plug; a. cleaning solution storage port 1; b. cleaning solution storage port 2; c. cleaning solution storage port 3; d. cleaning solution storage port 4; e. pyrolysis liquid storage tube.

DESCRIPTION OF THE EMBODIMENTS

The present invention will be further described below with reference to the accompanying drawings and embodiments. In the specific implementation process, as shown in FIGS. 1, 2, 3, 4, 5, 6 and 11, a nucleic acid test kit comprises a lower circular fixing cover 1. A circular kit 2 is mounted on the inner side of the lower circular fixing cover 1. A scaling film 3 is arranged at a top of the circular kit 2, and a lower lid 4 is arranged at a lower end of the sealing film 3. The scaling film 3 is made of latex. The lower lid 14 is made of plastic. A bottom of the lower lid 4 is connected with and pressed against the lower end of the sealing film 3, and a bottom of the sealing film 3 is pressed against the top of the circular kit 2. First bolts 5 are rotatably connected to an outer side of the lower circular fixing cover 1 in an equidistant manner through bearings, and the first bolts 5 are in threaded connection with the lower lid 4 through first threaded holes. A middle part of the circular kit 2 is provided with a metal bar storage hole 6, and an upper cover 7 is arranged above the sealing film 3; and one side of the circular kit 2 is provided with a sample adding port 8. A rubber plug 9 is connected to a middle part of the sample adding port 8 in an interference manner. A metal bar 10 is fixed to a middle part of the upper cover 7, and a lower end of the metal bar 10 is inserted into the metal bar storage hole 6. The metal bar 10 is embedded into the upper cover 7 during injection molding. Alternatively, the upper cover 7 may be bonded to the metal bar 10 after being manufactured. An upper circular fixing cover 11 is fixed to an outer wall of the upper cover 7. An upper end of the sealing film 3 is provided with an upper lid 12 made of latex, a top of the upper lid 12 is connected with and pressed against the upper end of the sealing film 3, and a top of the sealing film 3 is pressed against a bottom of the upper cover 7. 3M double-sided adhesive tape is attached to the sealing film 3 at 45 degrees (or other angles) to increase friction and prevent the sealing film 3 from being pulled off due to thinning when the upper cover 7 is pulled. Second bolts 13 are rotatably connected to an outer ring of the upper circular fixing cover 11 through bearings in an equidistant manner, and the second bolts 13 are in threaded connection with the upper lid 12 through second threaded holes. One side of the circular kit 2 is provided with pre-embedded tube assembly holes 14, a bottom of the circular kit 2 is fixedly provided with PCR tubes 15 located outside the pre-mounting hole 14, and a pre-embedded tube component 16 is arranged in an inner side of the mounting hole 14. A side, away from the PCR tubes 15, of the circular kit 2 is provided with shallow tubes 17 in an equidistant manner, and a U-shaped aluminum foil film 18 is arranged on a side, close to the shallow tubes 17, of the top of the circular kit 2. The U-shaped aluminum foil film 18 is configured for encapsulation storage, and during the use of the kit for detection, a probe can be used to puncture the U-shaped aluminum foil film 18. The U-shaped aluminum foil film 18 can then stretch to form a hole having a size larger than the diameter of the metal bar 10 such that the U-shaped aluminum foil film 18 does not affect the up-and-down linear movement of the metal bar 10. The aluminum foil film material for encapsulation may also be other plastic films. A first connecting mechanism 19 is fixed to a bottom of the lower circular fixing cover 1 and configured for driving the first bolts 5 to rotate simultaneously. A second connecting mechanism 20 is connected to a top of the upper circular fixing cover 11 and configured for driving the second bolts 13 to rotate simultaneously. A detection hole 27 is formed in one side of the upper cover 7, and a detection plug 28 is connected to an inner wall of the detection hole 27 in an interference-fit manner.

It should be noted that the nucleic acid test kit provided by the invention greatly improves the efficiency of encapsulating nucleic acid detection reagents, and makes it easier for people to operate. Meanwhile, it can perform air leakage detection at the end of encapsulation, significantly enhancing the quality of encapsulation compared to traditional detection kits.

Figure 7:
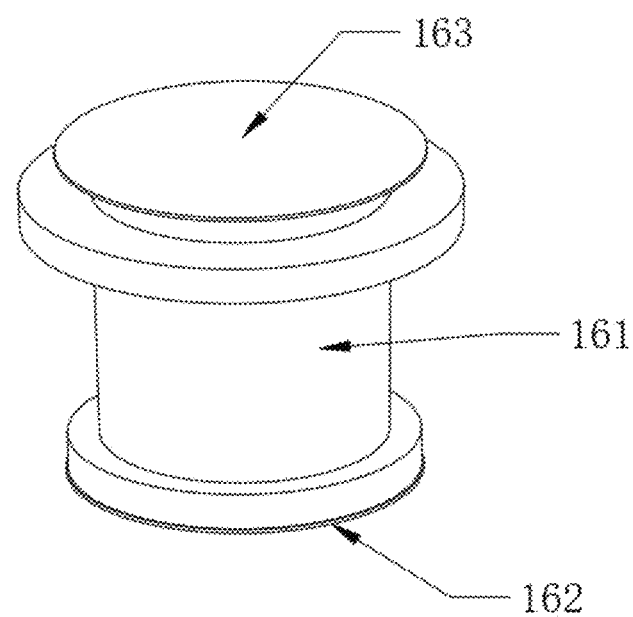
FIG. 7 is a structural diagram of an pre-embedded tube component according to the invention.

Referring to FIG. 7, the pre-embedded tube component 16 comprises an embedded tube body 161, an aluminum foil film 162 and an aluminum foil film 163. The embedded tube body 161 is arranged on an inner wall of the mounting hole 14, the aluminum foil film 162 is connected to a bottom of the embedded tube body 161 by heat seal, the aluminum foil film 163 is connected to a top of the embedded tube body 161 by heat seal. A bottom of the aluminum foil film 162 is pressed against a top of the PCR tube 15.

It should be noted that the liquid or solid reagent in the PCR tube 15 is sealed by pressing the aluminum foil film 162 against an upper step of the PCR tube 15, and a scaling material may added between the step and the aluminum foil film 162. After being pressed into the circular kit 2, the pre-embedded tube component 16 can be fixed to the circular kit 2 through welding, bonding, interference-fit and other methods.

Figure 8:
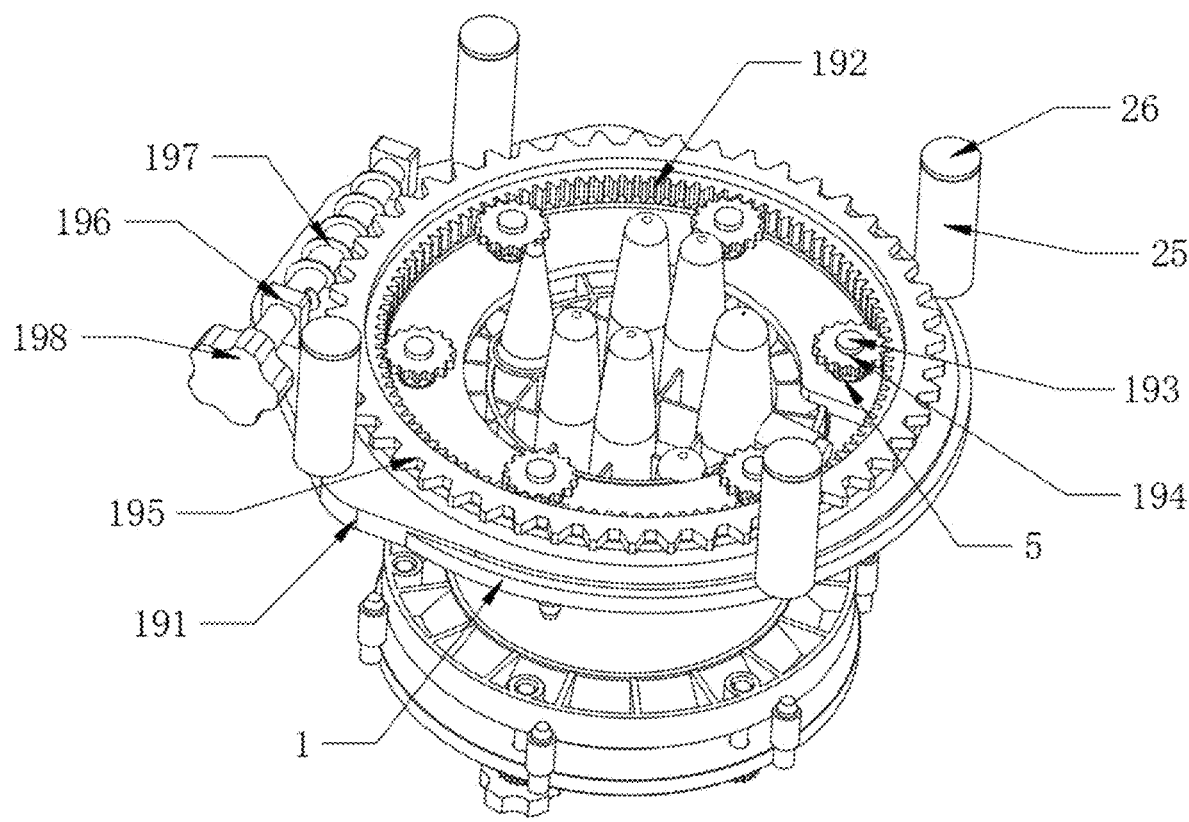
FIG. 8 is a structural diagram of a first connecting mechanism according to the invention.

Referring to FIG. 8, the first connecting mechanism 19 comprises a bottom connecting plate 191, an internal ring gear 192, first connecting shafts 193, first gears 194, a worm gear ring 195, supporting blocks 196, a worm 197 and a first rotating wheel 198. The bottom connecting plate 191 is fixed to a bottom of the lower circular fixing cover 1, the internal ring gear 192 is rotatably connected to a lower surface of the bottom connecting plate 191 through a bearing, the first connecting shaft 193 is fixed to a middle part of a lower surface of the first bolt 5, and the first gear 194 is fixed to a middle part of the first connecting shaft 193. The six first gears 194 are meshed with internal teeth of the internal ring gear 192, and the worm gear ring 195 is fixed to a bottom of the internal ring gear 192. A pair of supporting blocks 196 are symmetrically fixed to one side of a lower surface of the bottom connecting plate 191, the worm 197 is rotatably connected between the two supporting blocks 196 through bearings, the worm 197 is meshed with the worm gear ring 195, and one end of the worm 197 passes through one of the supporting blocks 196 to be fixed with the first rotating wheel 198.

Referring to FIG. 1, first positioning columns 21 are fixed to a top of the lower circular fixing cover 1 in an equidistant manner, first positioning sleeves 22 are fixed to an outer wall of the lower lid 4 in an equidistant manner, and the first positioning columns 21 are fitted into the first positioning sleeves 22 for positioning the lower lid 4 during the pressing process.

Figure 9:
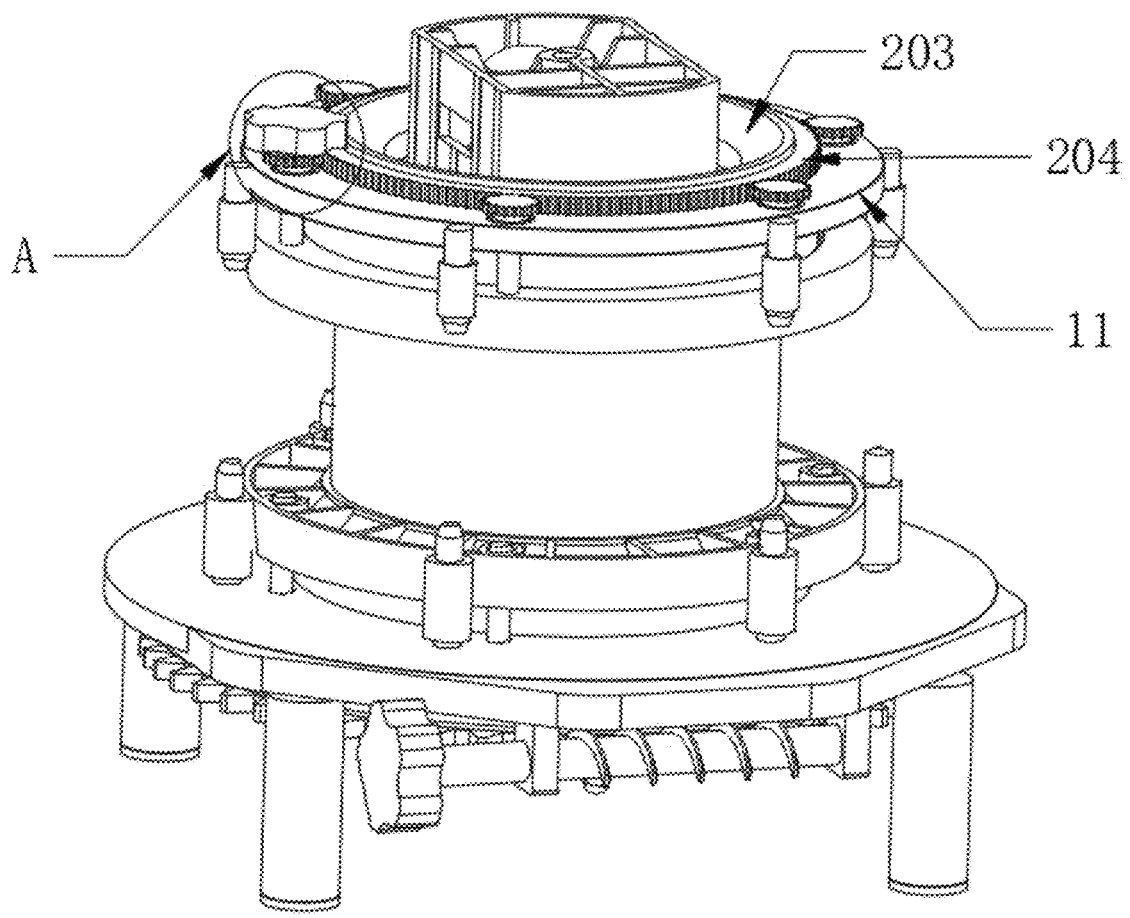
FIG. 9 is a structural diagram of a second connecting mechanism according to the invention.
Figure 10:
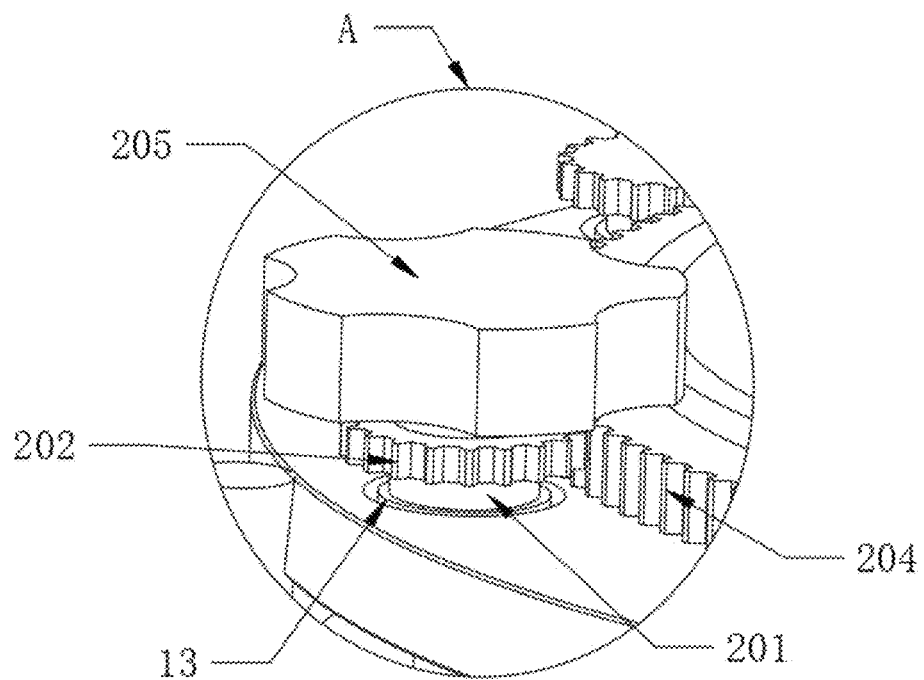
FIG. 10 is an enlarged view of part A of FIG. 9.
Figure 11:
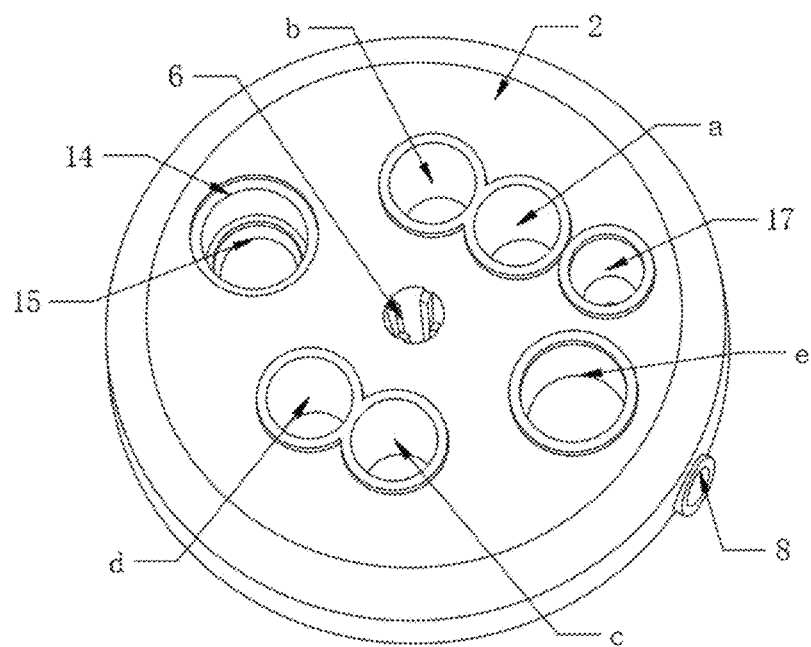
FIG. 11 is a schematic diagram of the position and structure of a shallow tube according to the invention.

Referring to FIGS. 9 and 10, the second connecting mechanism 20 comprises second connecting shafts 201, second gears 202, a rotating ring 203, a external ring gear 204 and a second rotating wheel 205. The second connecting shaft 201 is fixed to a middle part of an upper surface of the second bolt 13, and the second gear 202 is fixed to an upper end of the second connecting shaft 201, and the rotating ring 203 is rotatably connected to a middle part of an upper surface of the upper circular fixing cover 11 through a bearing, the external ring gear 204 is fixed to an outer wall of an upper end of the rotating ring 203, the six second gears 202 are meshed with the external ring gear 204, and the second rotating wheel 205 is fixed to a top of one of the second connecting shafts 201 on one side of the upper circular fixing cover 11.

It should be noted that the first connecting mechanism 19 and the second connecting mechanism 20 can drive the first bolts 5 or the second bolts 13 to rotate by rotating the first rotating wheel 198 and the second rotating wheel 205 when the sealing film 3 is pressed, thus greatly improving the encapsulation efficiency and making it convenient for people to use.

Besides the above-mentioned connection ways, the plastic/latex lid may also be pressed by replacing the upper and lower circular fixing covers with plastic materials, and then welding the upper and lower latex/plastic covers with the upper and lower circular fixing covers by means such as ultrasonic welding.

As shown in FIG. 1, second positioning columns 23 are fixed to an outer wall of the upper circular fixing cover 11 in an equidistant manner, second positioning sleeves 24 are fixed to an outer wall of the upper lid 12 in an equidistant manner, and the second positioning columns 23 are fitted into the second positioning sleeves 24 for positioning the upper lid 12 during the pressing process.

Referring to FIGS. 8 and 10, the first rotating wheel 198 and the second rotating wheel 205 are both configured with a plum blossom shape, allowing people to easily rotate the first rotating wheel 198 or the second rotating wheel 205.

Referring to FIG. 1, a top of the first positioning column 21 and a bottom of the second positioning column 23 are both provided with chamfers, which facilitates the insertion of the first positioning columns 21 into the first positioning sleeves 22 and the second positioning columns 23 into the second positioning sleeves 24.

Referring to FIG. 8, supporting columns 25 are fixed to a bottom of the bottom connecting plate 191 in an equidistant manner, and a rubber friction pad 26 is fixed to a bottom of the supporting column 25, so that the bottom connecting plate 191 can be placed stably.

Further, the sealing film 3 comprises an elastic film or a non-elastic film. In this application, the sealing film 3 is preferably made of a non-elastic film instead of an elastic film. On the one hand, the non-elastic film is more easily attached to the top of the circular kit 2, forming a more airtight sealing environment; on the other hand, the cost of non-elastic films is lower.

The invention further provides a preparation process of the nucleic acid test kit, comprising the following steps:
(1) sealing the sample adding port 8 with the rubber plug 9, and encapsulating a nucleic acid extraction reagent and magnetic beads in the circular kit 2 with the U-shaped aluminum foil film 18, wherein the nucleic acid extraction reagent and the magnetic beads are placed in corresponding storage ports of the circular kit 2, the magnetic beads being able to be replaced with magnetic bead liquid, the extraction reagent being lysis solution, cleaning solution 1, cleaning solution 2, cleaning solution 3 and cleaning solution 4, the lysis solution being placed in a lysis solution storage tube e, and the cleaning solutions 1 to 4 being respectively placed in a cleaning solution storage port a, a cleaning solution storage port b, a cleaning solution storage port c and a cleaning solution storage port d;
(2) adding liquid or solid reagents into the PCR tube 15, and then the pre-embedded tube component 16 being pressed into the mounting hole 14, the order of steps 1 and 2 being reversible;
(3) bonding the sealing film 3 to the top of the circular kit 2 and the bottom of the upper cover 7, followed by pressing and securing, a desiccant being able to be placed at the bottom of the upper cover 7 in advance as required;
(4) introducing, via the detection hole 27 in the upper cover 7, air from an external air source into an interior space surrounded by the sealing film 3 to test the seal tightness of the sealing film 3; and
(5) if no leakage is detected, sealing the detection hole 27 in the upper cover 7 with the detection plug 28.

In a preferred embodiment of the invention, a desiccant is provided in the interior space of the sealing film 3, and the desiccant can be fixed on the upper cover 7 or a base without affecting the movement of the metal bar 10 and an encapsulating position of the reagent.

An outer wall thickness of the PCR tube 15 is 0.1-1.5 mm, and the light transmittance is not less than 60% to ensure that it is able to pass the optical detection.

An upper surface of the U-shaped aluminum foil film 18 does not react with the stored reagent, and a PP plastic film, which can be stored in contact with the liquid and solid in the shallow tubes 17, is attached to a lower surface of the U-shaped aluminum foil film 18. The aluminum foil film 163 at the top of the embedded tube body 161 is a single-sided contact reagent. The aluminum foil film 162 at the bottom is a double-sided contact reagent. The body 161 of the pre-embedded tube component 16 is sealed in the following order: first, the bottom of the body 161 being sealed by the bottom aluminum foil film 162, then the embedded reagent being fed into the body 161, and the top of the body 161 being sealed by the top aluminum foil film A 163. The bottom liquid or solid reagent is placed in the PCR tube 15, then the bottom surface of the aluminum foil film 162 is cleaned and the pre-embedded tube component 16 is placed in the hole 14. The pre-embedded tube component 16 is sealed to the top of the PCR tube 15 by pressing the aluminum foil film 162 and the step at the bottom of the pre-embedded tube component 16 against the top of the PCR tube 15. Alternatively, the pre-embedded tube component 16 is sealed to the bottom of the PCR tube 15 by tightly fitting the aluminum foil film 162 and the step at the bottom of the pre-embedded tube component 16 against an internal structure of the circular kit 2 at the top of the PCR tube 15. The pre-embedded tube component 16 can encapsulate the PCR tube 15 by crimping, that is, interference-fit, welding, or bonding. The step at the bottom of the pre-embedded tube component 16 can be designed as an arc-shaped step.

Working principle is as following: when in use, after the reagent, magnetic beads or magnetic bead liquid are put into the respective storage ports on the circular kit 2, the PCR tubes 15 are encapsulated by the pre-embedded tube components 16 respectively, and the shallow tubes 17 are encapsulated by the U-shaped aluminum foil film 18. After the encapsulation, the sealing film 3 is stuck on the circular kit 2; further, the lower lid 4 at the lower end of the sealing film 3 is pressed against the circular kit 2, the pressing process being as follows: by picking up the lower lid 4 and rotating the lower lid 4 to make the first positioning sleeves 22 on the lower lid 4 be aligned with the respective first positioning columns 21 on the lower circular fixing cover 1, then the lower lid 4 is moved downwards, so that the first positioning sleeves 22 are sleeved on the respective first positioning columns 21 to achieve the positioning of the lower lid 4. The upper end of the first bolts 5 are inserted into the first threaded holes. Then, the worm 197 is driven to rotate by rotating the first rotating wheel 198, and the worm 197 drives the worm gear ring 195 to rotate. The worm gear ring 195 can drive the inner gear ring 192 to rotate, and when the inner gear ring 192 rotates, it can drive the six first gears 194 to rotate simultaneously, further drive the first connecting shaft 193 to rotate, and further drive the six first bolts 5 to rotate at the same time. Since the first bolts 5 are in threaded connection with the first threaded holes, rotation of the first bolts 5 results in the lower lid 4 being pulled down by the first bolts 5, and finally the sealing film 3 is pressed on the circular kit 2 by the lower lid 4;

then the installation of the upper cover 7 and the pressing of the upper end of the sealing film 3 are carried out. Specifically, the upper cover 7 is picked up, the metal bar 10 on the upper cover 7 is inserted into the metal bar storage hole 6 in the middle part of the circular kit 2, and then the upper lid 12 outside the sealing film 3 is picked up to install the upper lid 12 as following: the six second positioning sleeves 24 on the upper lid 12 being aligned with the six second positioning columns 23 on the upper circular fixing cover 11 respectively, the upper lid 12 is moved up until the second positioning columns 23 are fit into the second positioning sleeves 24, and finally the lower ends of the second bolts 13 are inserted into the second threaded holes. Then the upper lid 12 and the upper circular fixing cover 11 are pressed firmly; then by rotating the second rotating wheel 205, the second connecting shaft 201 fixed to the second rotating wheel 205 is driven to rotate, so as to drive one second bolt 13 fixed to the second connecting shaft 201 to be fixed. When the second connecting shaft 201 rotates, it can drive the second gear 202 to rotate, so as to drive the external ring gear 204 to rotate, so that the six second gears 202 can rotate at the same time, thus driving the six second bolts 13 to rotate at the same time, which allows the second bolts 13 in threaded connection with the second threaded holes to pull the upper lid 12 upward until the upper lid 12 presses the sealing film 3 on the upper cover 7 firmly. Thus, the encapsulation work is completed. The detection plug 28 can be opened after the encapsulation is completed, whether the sealing film 3 leaks can be detected by introducing air through the detection hole 27. After the detection is completed, the detection plug 28 is tightened.

The invention greatly improves the encapsulation efficiency, and makes it easier for people to operate. Meanwhile, it can perform air leakage detection at the end of encapsulation, significantly enhancing the quality of encapsulation compared to traditional detection kits and improving encapsulation efficiency. Further, the nucleic acid test kit provided by the invention ensures a sealed environment of a nucleic acid test reagent device during the entire process, including nucleic acid extraction, amplification, and detection, reducing the risk of sample cross-contamination and effectively improving the nucleic acid testing efficiency. The above are only embodiments of the present invention, which do not limit the patent scope of the present invention.

Any equivalent structure or equivalent flow transformation made by using the contents of the specification and drawings of the present invention, or directly or indirectly applied to other related technical fields, are equally included in the patent protection scope of the present invention.

What is claimed is:
1. A nucleic acid test kit, comprising:
a lower circular fixing cover (1);
a circular kit (2) arranged on an inner side of the lower circular fixing cover (1), a middle part of the circular kit (2) being provided with a metal bar storage hole (6);
a sealing film (3) arranged at a top of the circular kit (2), and
a lower lid (4) arranged at a lower end of the sealing film (3), wherein a bottom of the lower lid (4) is pressed against the lower end of the sealing film (3), and a bottom of the sealing film (3) is pressed against the top of the circular kit (2);
first bolts (5) rotatably connected to an outer side of the lower circular fixing cover (1) in an equidistant manner through bearings, each of the first bolts (5) being in threaded connection with the lower lid (4) through a first threaded hole;
an upper cover (7) arranged above the sealing film (3); and
an upper circular fixing cover (11) fixed to an outer wall of the upper cover (7);
wherein one side of the circular kit (2) is provided with a sample adding port (8), a rubber plug (9) is connected to a middle part of the sample adding port (8) in an interference manner;
a metal bar (10) is fixed to a middle part of the upper cover (7), and a lower end of the metal bar (10) is inserted into the metal bar storage hole (6);
an upper end of the sealing film (3) is provided with an upper lid (12), a top of the upper lid (12) is pressed against the upper end of the sealing film (3), and a top of the sealing film (3) is pressed against a bottom of the upper cover (7);
second bolts (13) are rotatably connected to an outer ring of the upper circular fixing cover (11) in an equidistant manner, and the second bolts (13) are in threaded connection with the upper lid (12) through second threaded holes; and
one side of the circular kit (2) is provided with a mounting hole (14), a bottom of the circular kit (2) is fixedly provided with a PCR (Polymerase Chain Reaction) tube (15) located outside the mounting hole (14), and a pre-embedded tube component (16) is arranged in an inner side of the mounting hole (14); and a side, away from the PCR tube (15), of the circular kit (2) is provided with shallow tubes (17) in an equidistant manner, a U-shaped aluminum foil film (18) is arranged on a side, close to the shallow tubes (17), of the top of the circular kit (2), a detection hole (27) is formed in one side of the upper cover (7), and a detection plug (28) is connected to an inner wall of the detection hole (27) in an interference manner.

2. The nucleic acid test kit according to claim 1, wherein a first connecting mechanism (19) is fixed to a bottom of the lower circular fixing cover (1), the first connecting mechanism (19) is configured for driving the first bolts (5) to rotate simultaneously, a second connecting mechanism (20) is connected to a top of the upper circular fixing cover (11), and the second connecting mechanism (20) is configured for driving the second bolts (13) to rotate simultaneously.

3. The nucleic acid test kit according to claim 2, wherein the pre-embedded tube component (16) comprises an embedded tube body (161), another aluminum foil film (162) and further another aluminum foil film (163), the embedded tube body (161) is arranged on an inner wall of the mounting hole (14), the another aluminum foil film (162) is fixed to a bottom of the embedded tube body (161) by heat seal, the further another aluminum foil film (163) is fixed to a top of the embedded tube body (161) by heat seal, and a bottom of the another aluminum foil film (162) is pressed against a top of the PCR tube (15).

4. The nucleic acid test kit according to claim 3, wherein the first connecting mechanism (19) comprises a bottom connecting plate (191), an internal ring gear (192), first connecting shafts (193), first gears (194), a worm gear ring (195), supporting blocks (196), a worm (197) and a first rotating wheel (198); and
    the bottom connecting plate (191) is fixed to a bottom of the lower circular fixing cover (1), the internal ring gear (192) is rotatably connected to a lower surface of the bottom connecting plate (191), each of the first connecting shafts (193) is fixed to a middle part of a lower surface of a corresponding one of the first bolts (5), and each of the first gears (194) is fixed to a middle part of a corresponding one of first connecting shafts (193); the first gears (194) are meshed with the internal ring gear (192), and the worm gear ring (195) is fixed to a bottom of the internal ring gear (192); and the supporting blocks (196) are symmetrically fixed to one side of a lower surface of the bottom connecting plate (191), the worm (197) is rotatably connected between the two supporting blocks (196), the worm (197) is meshed with the worm gear ring (195), and one end of the worm (197) passes through the supporting blocks (196) and is fixed with the first rotating wheel (198).

5. The nucleic acid test kit according to claim 3, wherein first positioning columns (21) are fixed to a top of the lower circular fixing cover (1) in an equidistant manner, first positioning sleeves (22) are fixed to an outer wall of the lower lid (4) in an equidistant manner, and the first positioning columns (21) are fitted into the first positioning sleeves (22) respectively.

6. The nucleic acid test kit according to claim 5, wherein the second connecting mechanism (20) comprises second connecting shafts (201), second gears (202), a rotating ring (203), a gear ring (204) and a second rotating wheel (205);
    each of the second connecting shafts (201) is fixed to a middle part of an upper surface of a corresponding one of the second bolts (13), and each of the second gears (202) is fixed to an upper end of a corresponding one of the second connecting shafts (201);
    the rotating ring (203) is rotatably connected to a middle part of an upper surface of the upper circular fixing cover (11);
    the gear ring (204) is fixed to an outer wall of an upper end of the rotating ring (203);
    the second gears (202) are engaged with the gear ring (204); and
    the second rotating wheel (205) is fixed to a top of one of the second connecting shafts (201) on one side of the upper circular fixing cover (11).

7. The nucleic acid test kit according to claim 5, wherein second positioning columns (23) are fixed to an outer wall of the upper circular fixing cover (11) in an equidistant manner, second positioning sleeves (24) are fixed to an outer wall of the upper lid (12) in an equidistant manner, and the second positioning columns (23) are fitted into the second positioning sleeves (24) respectively, the first rotating wheel (198) and the second rotating wheel (205) are both configured in a plum blossom shape; and a top of the first positioning column (21) and a bottom of the second positioning column (23) are both provided with chamfers.

8. The nucleic acid test kit according to claim 3, wherein supporting columns (25) are fixed to a bottom of the bottom connecting plate (191) in an equidistant manner, and a rubber friction pad (26) is fixed to a bottom of the supporting column (25).

9. The nucleic acid test kit according to claim 1, wherein the sealing film (3) comprises an elastic film or a non-elastic film.

* * * * *